US006054036A

United States Patent [19]

Izmailov et al.

[11] Patent Number: 6,054,036

[45] Date of Patent: Apr. 25, 2000

[54] ELECTROPHORESIS GELS AND GEL HOLDERS HAVING FIBER SPACERS AND METHOD OF MAKING SAME

[75] Inventors: Alexandre M. Izmailov, Toronto; Paul Waterhouse, Copetown; Henryk Zaleski, Mississauga, all of Canada

[73] Assignee: Visible Genetics Inc., Toronto, Canada

[21] Appl. No.: 09/077,304

[22] PCT Filed: Dec. 12, 1996

[86] PCT No.: PCT/CA96/00832

§ 371 Date: Dec. 31, 1998

§ 102(e) Date: Dec. 31, 1998

[87] PCT Pub. No.: WO97/21995

PCT Pub. Date: Jun. 19, 1997

Related U.S. Application Data

[63] Continuation-in-part of application No. 08/571,297, Dec. 12, 1995, Pat. No. 5,618,398.

[51] Int. Cl.[7] .......... G01N 27/26

[52] U.S. Cl. .......... 204/616; 204/606

[58] Field of Search .......... 204/456, 465, 204/466, 606, 615, 616, 620, 461, 612; 382/129, 132; 356/344

[56] References Cited

U.S. PATENT DOCUMENTS

| | | | |
|---|---|---|---|
| 3,663,395 | 5/1972 | Strickler . | |
| 4,704,198 | 11/1987 | Ebersole et al. . | |
| 4,790,919 | 12/1988 | Baylor, Jr. . | |
| 4,811,218 | 3/1989 | Hunkapiller et al. . | |
| 4,823,077 | 4/1989 | Hanson . | |
| 4,863,647 | 9/1989 | Baylor, Jr. . | |
| 4,919,784 | 4/1990 | Yetman | 204/612 |
| 4,929,329 | 5/1990 | Danby et al. . | |
| 5,047,135 | 9/1991 | Nieman . | |
| 5,062,942 | 11/1991 | Kambara et al. . | |
| 5,071,531 | 12/1991 | Soane . | |
| 5,073,246 | 12/1991 | Chu et al. . | |
| 5,091,652 | 2/1992 | Mathies et al. . | |
| 5,092,973 | 3/1992 | Zare et al. . | |
| 5,108,179 | 4/1992 | Myers . | |
| 5,119,316 | 6/1992 | Dam et al. . | |
| 5,122,345 | 6/1992 | Tabor et al. . | |
| 5,141,868 | 8/1992 | Shanks et al. . | |
| 5,164,066 | 11/1992 | Yetman et al. . | |
| 5,186,807 | 2/1993 | Sanford et al. . | |
| 5,192,408 | 3/1993 | Scott . | |
| 5,192,412 | 3/1993 | Kambara et al. . | |
| 5,202,010 | 4/1993 | Guzman . | |
| 5,209,831 | 5/1993 | MacConnell . | |
| 5,324,401 | 6/1994 | Yeung et al. . | |
| 5,338,426 | 8/1994 | Shigeura et al. . | |
| 5,356,776 | 10/1994 | Kambara et al. . | |

FOREIGN PATENT DOCUMENTS

| | | |
|---|---|---|
| 0 294 524 | 12/1988 | European Pat. Off. . |
| 0 404 646 | 12/1990 | European Pat. Off. . |
| 0 504 943 | 9/1992 | European Pat. Off. . |
| 0 534 135 | 3/1993 | European Pat. Off. . |

OTHER PUBLICATIONS

JAPIO abstract of Takamori et al. (JP 02093360), Apr. 1990.

Josef Eisinger ("Visible Gel Electrophoresis and the Deterinaito of Association Constants", Biochem. Biophys. Res. Commun. (1971), 44(5), 1135–42, month unknown.

*Primary Examiner*—Jill Warden
*Assistant Examiner*—Alex Noguerola
*Attorney, Agent, or Firm*—Oppedahl & Larson LLP

[57] ABSTRACT

Gel holders for electrophoresis gels are made using clad fibers, particularly glass fibers as spacers between substrates. A plurality of fibers with a high-melting interior core and a low-melting external cladding are placed between a first planar substrate and a second planar substrate. The fibers are heated to a temperature sufficient to at least soften the exterior cladding of the fibers without softening the interior core of the fibers, and then cooled while they are in contact with the first and second substrates to solidify the exterior cladding. This adheres the fibers to the first and second substrates, and forms a gel chamber between said first and second substrates. The gel chamber has a thickness defined by interior core of the fibers. The fibers may be heated before or after the second substrate is placed over the top of the fibers. The gel holders thus formed may be filled immediately with a gel forming solution such as a polyacrylamide, or they may be stored indefinitely and used as needed.

4 Claims, 6 Drawing Sheets

50
43
61
EXCITATION/ DETECTION ZONE
FLUORESCENCE EMISSION
EXCITATION ENERGY

ELECTROPHORESIS GELS AND GEL HOLDERS HAVING FIBER SPACERS AND METHOD OF MAKING SAME

This application is a continuation-in-part of Ser. No. 08/571,297, filed Dec. 12, 1995, which is now U.S. Pat. No. 5,618,398.

BACKGROUND OF THE INVENTION

DNA sequencing may be carried out using automated systems designed for laboratory application. Methods and apparatus for sequencing of DNA are described in U.S. Pat. Nos. 4,811,218; 4,823,007; 5,062,942; 5,091,652; 5,119,316 and 5,122,345, which are incorporated herein by reference.

The general methodology employed in these systems involves breaking up the sample DNA using restriction endonucleases; amplifying (for example with PCR) the restriction fragment of interest; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

In performing a nucleic acid sequence analysis on a gel, the characteristics of the gel, including the size and thickness, impact the time and cost required to do the analysis. Since it is desirable to reduce the time and cost of sequencing analyses in order to improve the available of sequencing as a diagnostic tool, it would be advantageous to have a gel which permitted analysis of very small quantities of oligonucleotide fragments in a short period of time. It would further be advantageous to have a disposable, single use gel holder which could be manufactured on a large scale which when filled with a gel would provide these desirable characteristics.

Persons making the very thin gels which can achieve the type of short analysis times and high throughput desired for sequence analysis face several challenges. Significant among these is developing a fabrication technique which defines and maintains a very uniform spacing between the substrates surrounding the gel, so that the gel itself is of uniform thickness. U.S. Pat. Nos. 4,929,329 and 5,164,066, which are incorporated herein by reference, disclose the formation of electrophoresis gels using thin films (on the order of 0.10 to 0.02 inches thick), for example made from mylar, or nylon monofilaments as spacers between front and back plates. The spacers are not adhered to the plates, but are simply placed between the two plates and held in place using clamps while the space between the two plates is filled with gel forming solution. After polymerization, the polymerized gel holds the two plates, as well as the spacers in place.

The method of forming electrophoresis gels disclosed in these patents has several drawbacks. First of all, because the spacers have to be positioned and then held in place during the gel-filling operation, the resulting gels are not well suited to large scale production. Furthermore, because gels have short shelf lives, once prepared, and because it is the gel which holds the plates and the spacers together, assembly of the device must occur at the point of use. This too argues against the use of spacers as disclosed in these patents in the production of significant numbers of gels, or in the production of disposable, single use gel holders.

It an object of the present invention to provide disposable, single use gel holders having a very thin gel chamber of uniform thickness, which can be easily manufactured.

It is a further object of this invention to provide a method of making disposable, single use gel holders having a very thin gel chamber of uniform thickness, which can be easily manufactured.

It is a further object of this invention to provide electrophoresis gels formed within disposable, single use gel holders having a very thin gel chamber of uniform thickness, which can be easily manufactured.

SUMMARY OF THE INVENTION

These and other objects of the invention can be achieved by forming a gel holder for an electrophoresis gel using clad fibers, particularly glass fibers as spacers between the substrates. Thus, one aspect of the invention is a method comprising the steps of:

(a) placing a plurality of fibers between a first planar substrate and a second planar substrate, said fibers having an interior core having a first melting point and an external cladding having a second melting point lower than the first melting point;

(b) heating the fibers to a temperature sufficient to at least soften the exterior cladding of the fibers without softening the interior core of the fibers; and (c) cooling the heated fibers while they are in contact with the first and second substrates to resolidify the exterior cladding and to adhere the fibers to the first and second substrates, thereby forming a gel chamber between said first and second substrates, said gel chamber having a thickness defined by interior core of the fibers. The fibers may be heated before or after the second substrate is placed over the top of the fibers. The gel holders thus formed may be filled immediately with a gel forming solution such as a polyacrylamide, or they may be stored indefinitely and used as needed.

Further aspects of the invention are gel holder, and electrophoresis gel products comprising (a) a first planar substrate;

(b) a second planar substrate; and (c) a plurality of fibers disposed between the first and second planar substrates. The fibers are adhered to the first and second planar substrates with a melt-flowed substance having a lower melting temperature than the fibers so that the fibers and the first and second planar substrates, in concert, define a gel chamber having a thickness defined by the diameter of the fibers. In the finished electrophoresis gel, this chamber is filled with a polymerized gel such as a polyacrylamide gel.

DETAILED DESCRIPTION OF THE INVENTION

Figure 1A:
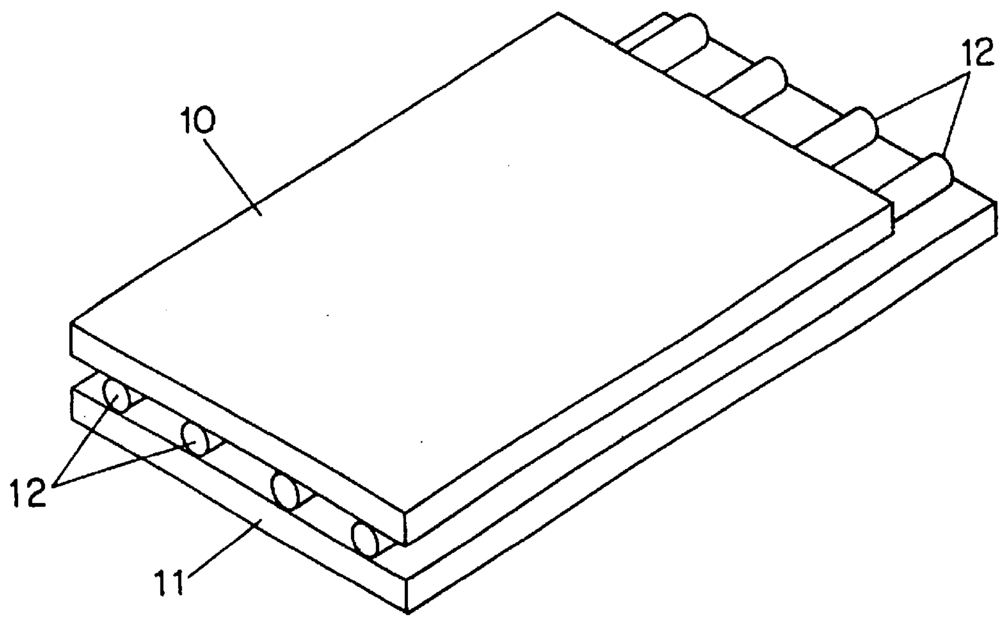
FIGS. 1A and 1B shows a first embodiment of a gel holder in accordance with the present invention.
Figure 1B:
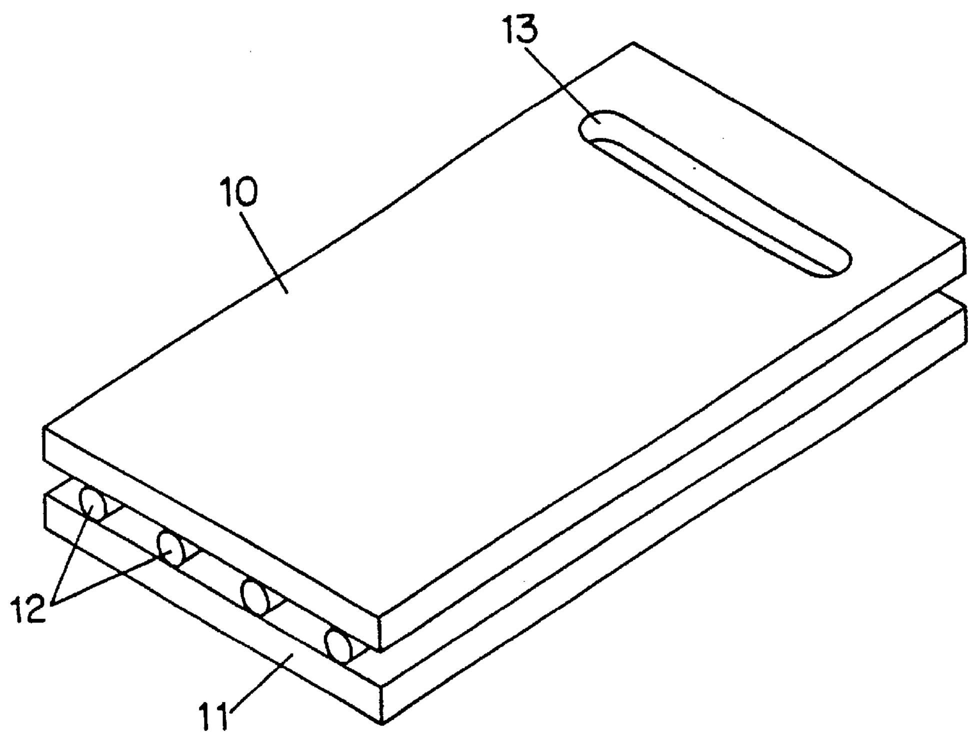

FIG. 1 shows a first embodiment of a gel holder in accordance with the present invention. The gel holder is formed from a top substrate 10, a bottom substrate 11 and a plurality of fibers 12. The fibers 12 are disposed parallel to one another and to opposing edges of the substrates 10, 11 and extend from one end of the substrates to the other. The bottom substrate 11 may extend beyond the top substrate 10 at one end of the gel holder as shown to facilitate loading of electrophoresis samples, in which case the fibers may end even with the top substrate or extend out onto the bottom substrate as shown in FIG. 1A. Alternatively, an opening 13 may be cut near one end of the top substrate for this purpose. (FIG. 1B).

Figure 2:
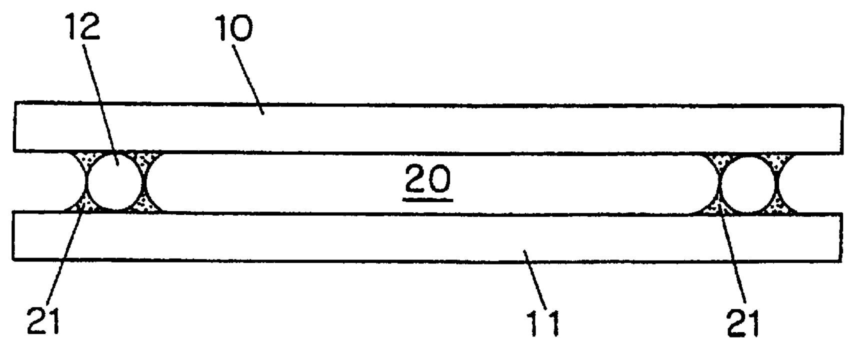
FIG. 2 shows an end view of a gel holder in accordance with the invention.

FIG. 2 shows the bottom end of a gel holder having two fibers rather than the four shown in FIG. 1 in greater detail. The fibers 12 are in contact with the top and bottom substrates 10, 11, and are adhered to the substrates with a melt-flowed substance 21. The fibers 12 and the top and bottom substrates 10, 11 in concert define a chamber 20 which is filled with an electrophoresis gel.

As used in the specification and claims hereof, the term "melt-flowed substance" refers to a material which has been at least softened and preferably melted to allow it to conform to the shape of surrounding unmelted materials, and then resolidified in the conformed shape to adhere the surrounding objects together.

Figure 3:
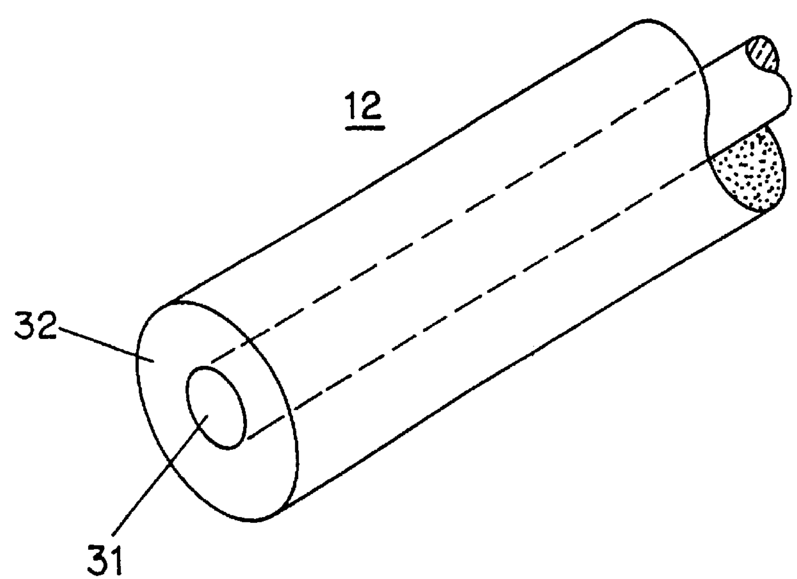
FIG. 3 shows two-layer fibers useful in the present invention.

The gel holder of the invention can be made by using fibers as shown in FIG. 3 having an interior core 31 having a first melting point and an external cladding 32 having a second melting point lower than the first melting point. The fibers may have a circular cross-section as shown in FIG. 3, or other shapes including ovoid and rectangular. Preferably, the fibers are glass fibers. In this case, the interior core is suitably made from glass having a melting point of from 600 to 800° C., while the exterior cladding is made from glass having a melting point of from 400 to 500° C. It will be appreciated, however, that other materials can be used for either the core fiber or the external cladding, or both. The core fiber can be made from glass, quartz or any polymer with a sufficiently higher melting point then the external cladding, such that the external cladding will melt while the core does not. The external cladding may be made of glass or a polymer, for example plastics, provided that the material does not negatively impact on the ability of a gel to polymerize within the chamber or fluoresce strongly at the wavelength used for detection of separated materials during or after electrophoresis.

In addition to having appropriate differences in melting temperature, it is also desirable to use fibers in which the coefficients of thermal expansion of the interior core 31 and the exterior cladding 32 are closely matched to reduce cracking or other deformations upon cooling. Preferably, the coefficients of thermal expansion are within 10% of each other. More preferably, the coefficients of thermal expansion are within 1% of each other.

The substrates used in forming the gel holders of the present invention may be any flat, planar material which is compatible with the electrophoresis gel and the method of detection to be employed. Thus, in some cases, plastic materials which do not interfere with the polymerization of the electrophoresis gel or the observation of the separated fragments on the electrophoresis gel can be used. Preferably, however, the substrates are made from glass, and most preferably from low-fluorescing glass. 1 mm Borosilicate glass which has greater ultraviolet light transparency is another preferred material.

Figure 4:
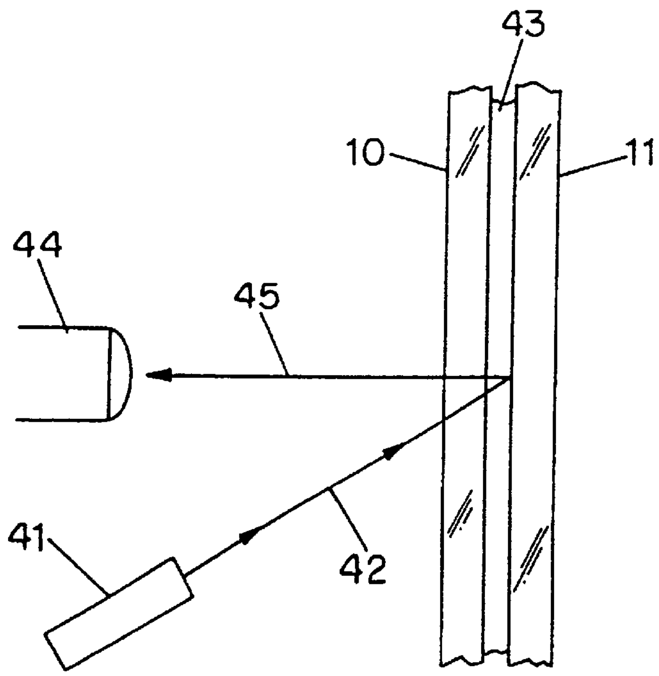
FIG. 4 shows an embodiment of the invention useful in apparatus where the interrogating beam and the detection system are on the same side of the gel.

At least one of the substrates used in forming the gel holder of the invention must be made from a material which will permit observation of the materials separated within the electrophoresis gel. In some apparatus, however, the interrogating beam source, for example a laser 41 producing a beam of light 42 for exciting fluorescent molecules in the gel 43, and the detector 44 for detecting emitted light 45 are located in the same side of the electrophoresis gel as shown in FIG. 4. In this case, the bottom substrate 11 can be selected to minimize any contribution to background radiation rather than for its ability to permit observation of the sample. For example, in the case of a gel holder intended for use in a sequencing apparatus with a fluorescence detection system, the bottom substrate 11 can be made from a colored glass which absorbs all of the exciting light which reaches it, and which thus is essentially non-fluorescent. Since background fluorescence arises in large part from fluorescent impurities in the substrates, this can substantially reduce the amount of background fluorescence and improve the sensitivity of the observations.

Figure 5:
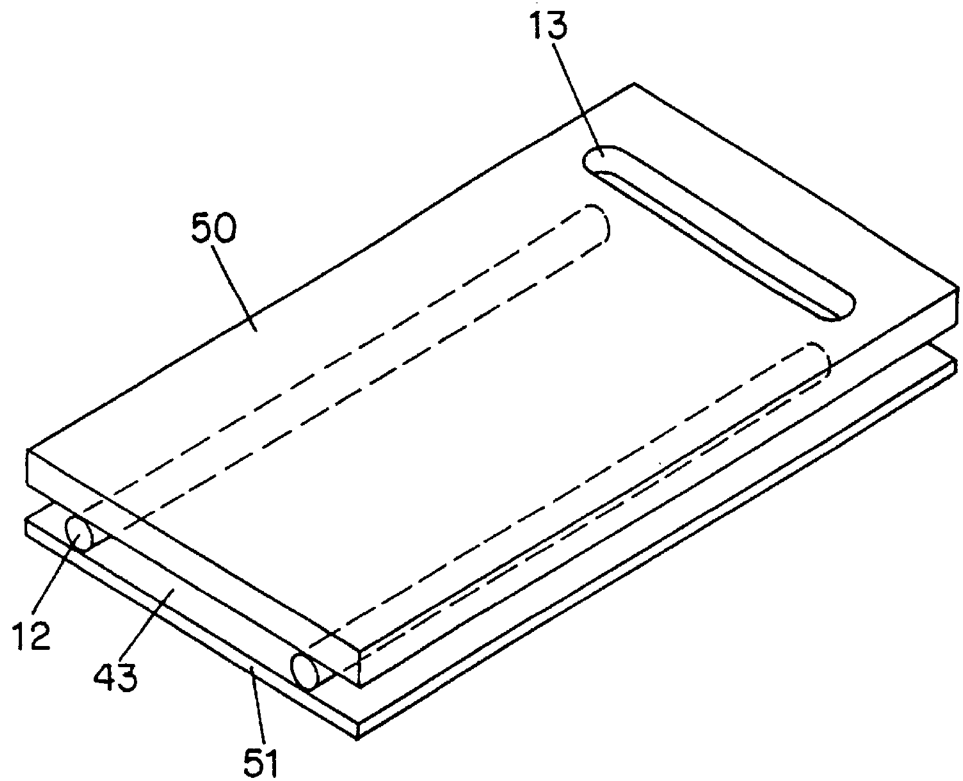
FIG. 5 shows an electrophoresis gel according to the invention.
Figure 6A:
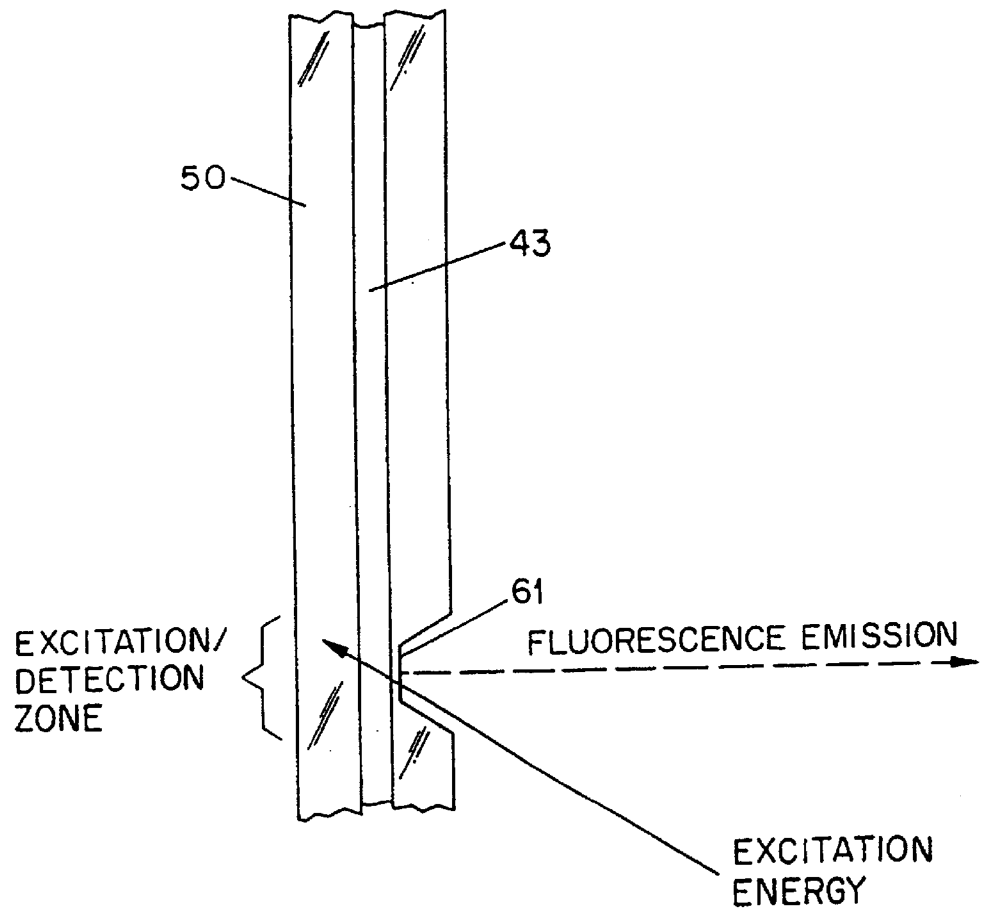
FIGS. 6A and 6B show the use of thin regions in gel holders according to the invention.
Figure 6B:
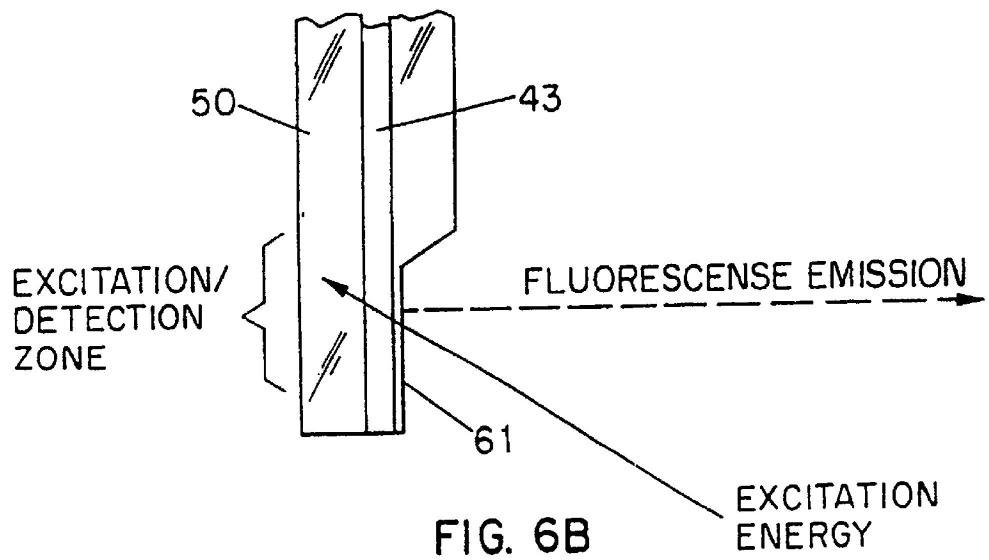
Figure 7A:
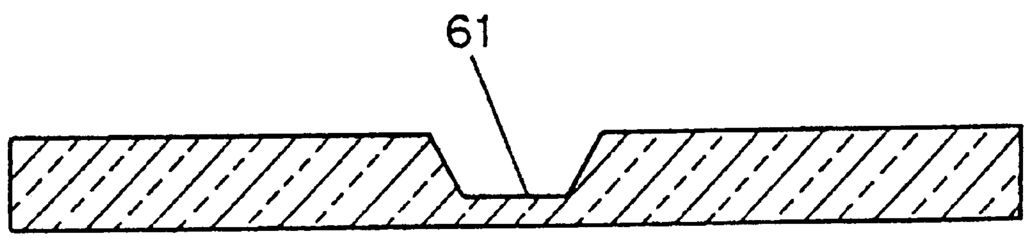
FIGS. 7A and 7B show construction alternatives for substrates with thin regions.
Figure 7B:
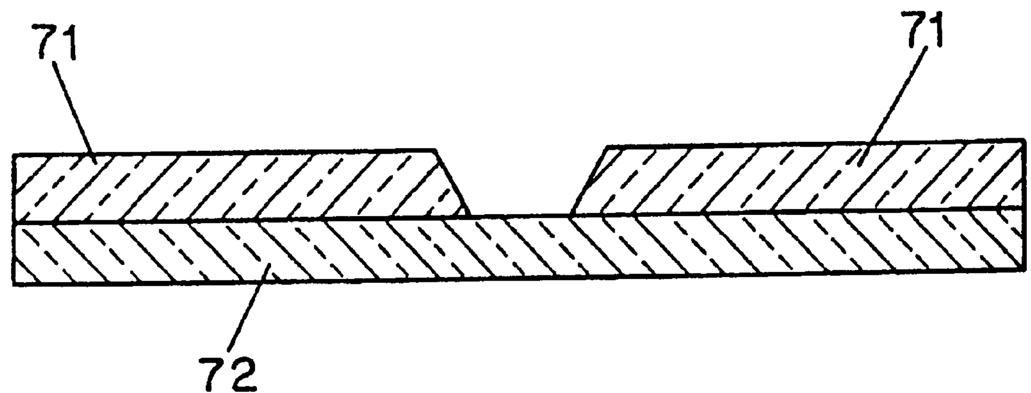

Another approach to reducing the background fluorescence is to utilize thinner substrates for the transparent substrate. For example, as shown in FIG. 5, one substrate 50 can be made of thicker (and preferably absorbing and non-fluorescing) material while the other substrate 51 is made of a very thin (i.e., 0.1 mm or less) transparent, low fluorescing material. Suitable thin materials include "cover slip" glass. The thin region 61 may also be localized to just an excitation/detection zone running perpendicular to the fibers as shown in FIG. 6A, or cover one edge of the gel as shown in FIG. 6B. Such substrates can be formed by molding a contiguous substrate into the desired shape (FIG. 7A), or by affixing blocks 71 of thicker materials onto a continuous thin substrate 72 (FIG. 7B). In the latter case, the blocks 71 of thicker material may also be formed from absorbing, non-fluorescing materials to further reduce background fluorescence.

To form the gel holder, the fibers are first placed onto a surface of one of the substrates. The substrates should be aligned parallel to one another and parallel to two opposing edges of the substrate. Fibers can be placed in a frame which will keep them parallel to each other and positioned at a certain distance from each other. If two fibers are used, they are advantageously placed near the edges of the substrate, thus creating one large gel chamber in the interior. More than two fibers may be used, in which case the gel chamber is divided into several parts. In this instance, fibers are preferably placed at intervals such that each part of the chamber is large enough to receive four samples, i.e., one sample lane for each chain terminating oligonucleotide mixture used in the sequencing process. Thus, in a gel intended to have 16 lanes (4 complete sequences), a total of five fibers would be used. The use of more than two fibers is particularly suitable for wider gels since the interior fibers help prevent sagging of the substrate in the middle of the gel chamber and thus define a gel chamber of more consistent width.

In one embodiment of the method of the invention, the next step is to place the second substrate over the fibers to form a sandwich structure in which the fibers are disposed between the two substrates. The sandwich is then heated, for example in an oven, to soften or melt the cladding on the fiber while pressure is applied to the exterior of the sandwich. As a result, the interior cores of the fibers are pressed into intimate contact with the substrates while the softened exterior cladding flows to fill the space around the fiber. Upon cooling the melt-flowed cladding material adheres the fibers to the substrates to form a gel holder. Fibers which extend beyond the edge of the sandwich can be trimmed off with clippers or by other means.

Figure 8:
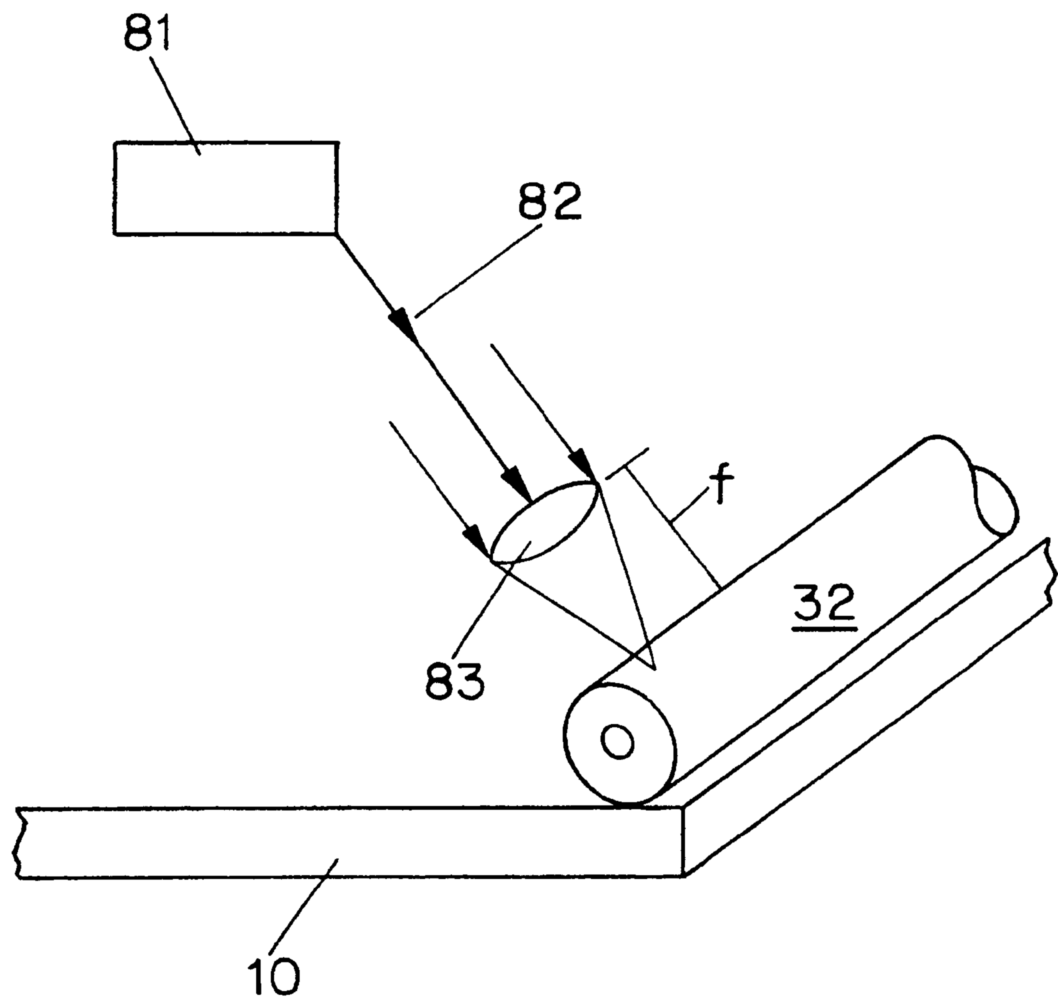
FIG. 8 shows the use of a laser to heat the exterior cladding of a fiber in a method according to the invention.

In a second embodiment of the method of the invention, the exterior cladding of the fibers is softened or melted prior to placing the second substrate over the fibers. For example, as shown in FIG. 8, a $CO_2$ laser 81 emits light 82 which is focused by lens 83 to heat the exterior cladding 32. The second substrate is then placed on top of the partially melted fibers, and the substrates are pressed together and allowed to cool.

In addition to the use of radiant heating, as in an oven, or focused laser heating, the cladding may be melted using radio frequency or microwave radiation. In this case, it may be desirable to dope the cladding with a susceptor molecule, for example lead oxide or other metals, to facilitate localized heating of the cladding.

The size of the gel chamber in the gel holders of the invention is determined by the thickness of the interior core of the fibers. For applications in rapid sequencing of nucleic acids, these fibers will preferably have a diameter of 250 microns or less, and most preferably of 50 to 100 microns. It will be appreciated, however, that the lower limit is fixed only by the ability to obtain a very thin fiber of consistent core diameter and the ability to uniformly introduce a gel forming solution without bubble formation into significantly smaller gaps. In fact, the present invention provides a very facile way to achieve very small spacings between the substrates, regardless of the size of the gap. Similarly, it will be appreciated that the method of the invention can be used to make gel holders having a larger gap. Such gel holders are not as well suited to high speed analysis of nucleic acid fragments, however.

The thickness of the exterior cladding is not critical provided that it contains enough material to adhere the fiber to the substrate(s) and is not so large as to block significant portions of the gel chamber. In general, claddings which are 5 to 10 microns thick are suitable.

Once the gel holder has been formed using either of the methods described above, the next steps are the filling of the chamber with a gel forming solution and the polymerization of the solution to form a gel. This process can be performed in any of a number of ways which will be apparent to persons skilled in the art. Preferably, the gel holder is filled using an apparatus of the type described in U.S. patent application Ser. No. 08/332,892, filed Nov. 1, 1994, and International Patent Application No. PCT/US95/13954 filed Oct. 31, 1995 and published as WO 96/13715, which applications are incorporated herein by reference.

In a third embodiment of the invention, the gel is placed in the chamber prior to the application of the second substrate over the fibers. In this embodiment, the fibers are placed over the first substrate, which may be light absorbing and non-fluorescing, and heated to adhere them to the substrate. A gel forming solution is then poured onto the substrate to essentially the same depth as the fibers and polymerized under an inert gas, e.g., nitrogen or argon. Temporary glass plates may be attached from the sides to prevent the gel from running off. Alternatively, a frame may be used which tightly seals the edges into which the bottom substrate is positioned before and during the polymerization process.

Because the top surface of the gel is free, this method provides a gel with very uniform thickness. After the gel is polymerized, a very thin (i.e,. 1 to 10 microns), flexible and transparent film is laid onto the top of the gel and secured by adhesive or mechanical means. Suitable materials for use as the cover film include any dissolved polymers, and particularly those which are sprayable. These polymer films will not affect polymerization of the gel, since the process of polymerization is finished before the film is attached.

The gel holders and electrophoresis gels of the present invention provide several advantages over the prior art. First, they are easy to manufacture, and can be prepared as disposable units for later filling with an electrophoresis gel. Second, they provide highly uniform spacing between the substrates. In addition, because the melt-flowed material is molded into shape thermally, materials such as glass which do not interfere with the polymerization of the gel or fluoresce strongly can be used to adhere the gel holders together.

What is claimed is:

1. An electrophoresis gel holder for use in an electrophoresis apparatus having a fluorescence detection system in which a light of an excitation wavelength is directed to an excitation/detection zone and light of an emission wavelength is detected when fluorescent substances are present in the excitation/detection zone, comprising (a) a planar first substrate;

(b) a planar second substrate; and (c) a spacer disposed between the first substrate and the second substrate, said substrates and said spacer in concert defining a gel chamber having a thickness defined by the spacer, wherein the first substrate is formed from a material which is optically transparent at the excitation and emission wavelengths at least in the region of the excitation/detection zone, and the second substrate is formed from a material which absorbs light at least at the excitation wavelength and is non-fluorescent when illuminated with the excitation wavelength.

2. The gel holder of claim 1, wherein the first substrate is thinner than the second substrate.

3. The gel holder of claim 1, wherein the first substrate is thinner than the second substrate in a localized region aligned with the excitation/detection zone.

4. The gel holder of claim 1, wherein the first substrate absorbs light of the excitation wavelength at regions remote from the localized region aligned with the excitation/detection zone.

* * * * *